United States Patent [19]

Rajadhyaksha et al.

[11] 4,038,415
[45] July 26, 1977

[54] PROSTAGLANDIN DEHYDROGENASE INHIBITING AGENTS

[75] Inventors: Vithal J. Rajadhyaksha, Mission Viejo, Calif.; Richard A. Schroer, West Nyack, N.Y.; Phillip J. Brock, Mountain View; Earl R. Krueger, Anaheim, both of Calif.

[73] Assignee: Nelson Research & Development Company, Irvine, Calif.

[21] Appl. No.: 719,432

[22] Filed: Sept. 1, 1976

Related U.S. Application Data

[62] Division of Ser. No. 602,736, Aug. 7, 1975, abandoned.

[51] Int. Cl.$^2$ .................. A61K 31/19; A61K 31/12; A61K 31/165
[52] U.S. Cl. .................. 424/317; 424/324; 424/330; 424/331
[58] Field of Search .............. 424/331, 330, 324, 317

[56] References Cited

U.S. PATENT DOCUMENTS

| | | | |
|---|---|---|---|
| 3,928,421 | 12/1975 | Kyogoku et al. | 424/331 |
| 3,965,190 | 6/1976 | Giudicelli et al. | 424/331 |

*Primary Examiner*—Sam Rosen
*Attorney, Agent, or Firm*—Martin A. Voet

[57] ABSTRACT

Novel prostaglandin dehydrogenase inhibiting agents having the structural formula

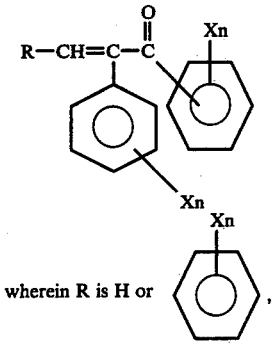

wherein R is H or phenyl, X is hydroxyl, dialkylaminomethyl, lower alkyl, lower alkoxy, aryl, substituted aryl, halogen, cyano, nitro, trihaloalkyl, —NR$_1$R$_2$ or —NHCOR$_1$ where R$_1$ and R$_2$ are hydrogen, lower alkyl or NH$_2$ and $n$ is 0–5.

12 Claims, No Drawings

PROSTAGLANDIN DEHYDROGENASE INHIBITING AGENTS

This is a division, of application, Ser. No. 602,736, filed Aug. 7, 1975, now abandoned.

BACKGROUND OF THE INVENTION

1. Field of the Invention

This invention relates to novel compounds. More particularly, the present invention relates to compounds having prostaglandin dehydrogenase blocking activity.

2. Background of the Prior Art

Prostaglandins are local hormones related to fatty acids occurring naturally in the body which act mainly as intercellular and/or intraorgan regulators. Enzymes also exist naturally in the body which synthesize or inactivate the prostaglandins. Enzymes which synthesize the prostaglandins are known as prostaglandin synthetases. Enzymes which inactivate the prostaglandins are known as prostaglandin dehydrogenases. Many therapeutically useful compounds are known to act through the mechanism of blocking prostaglandin synthesis by interfering or blocking the prostaglandin synthetase e.g. indomethacin and aspirin. It would be desirable to identify a compound or family of compounds having prostaglandin dehydrogenase blocking activity in that desirable prostaglandin-induced activity could be sustained for longer periods of time by blocking or inhibiting the inactivating action of the prostaglandin dehydrogenase enzyme.

SUMMARY OF THE INVENTION

We have now unexpectedly discovered a family of novel compounds which are useful in selectively blocking or inhibiting the activity of the enzyme prostaglandin dehydrogenase.

This invention therefore relates to novel compounds having the structural formula

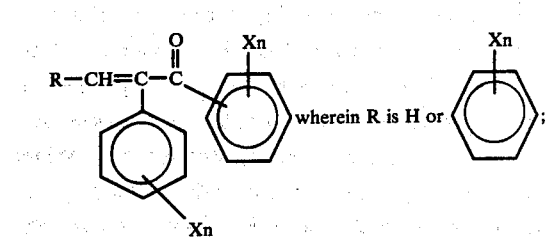

X is selected from the group consisting of hydroxyl, lower alkyl, lower alkoxy, aryl, substituted aryl, halogen, cyano, nitro, trihaloalkyl, $-NR_1R_2$ and $-NHCOR_1$, where $R_1$ and $R_2$ are selected from the group consisting of hydrogen, lower alkyl and $NH_2$] and $n$ is 0-5.

DETAILED DESCRIPTION OF THE INVENTION

The active compound of the present invention has the following structural formula

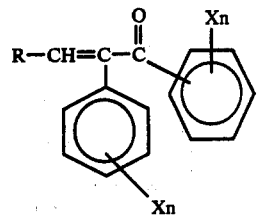

wherein R may be H or phenyl

X may be hydroxyl, lower alkyl or lower alkoxy, that is, straight or branch chain alkyl groups having 1-8 and preferably 1-4 carbon atoms, halogen, such as, for example, F, Cl, or Br; cyano, nitro trihaloalkyl such as $CF_3$, aryl, such as phenyl and substituted aryl, $-NR_1R_2$ and $-NHCOR_1$, where $R_1$ and $R_2$ are hydrogen, lower alkyl or $NH_2$, and n is 0 to 5.

A preferred embodiment of this invention relates to a 1-(4-hydroxyphenyl)-2,3-diaryl-2-propen-1-one having the following structural formula

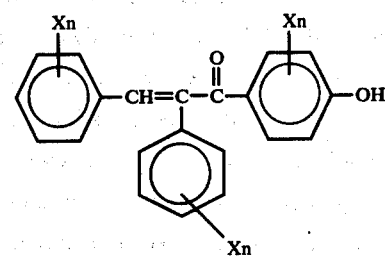

where X is H, halogen, $NO_2$, $CF_3$, lower alkyl, CN or amino and n is 1–4.

The foregoing class of compounds exhibits particularly good inhibitory activity against 15-OH prostaglandin dehydrogenase and represents a preferred subgroup of compounds within the scope of this invention.

The nuclear hydroxy substituted 1,2,3-triaryl-2-propen-1-one of this invention wherein R is aryl or substituted aryl are conveniently prepared by reacting an equimolar amount of a nuclear hydroxy substituted 1,2-diarylethanone with an equimolar amount of appropriately substituted aryl aldehyde in presence of piperidine at 30-60°. The condensation product thus obtained is then hydrolyzed by refluxing with glacial acetic acid. This is outlined in the scheme below.

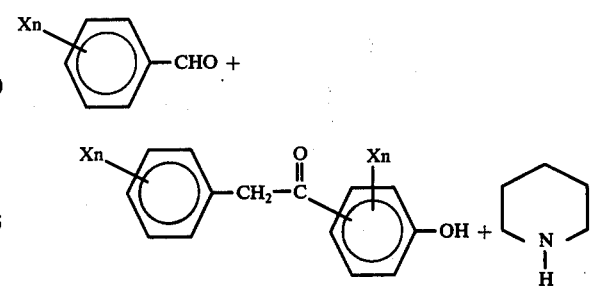

-continued

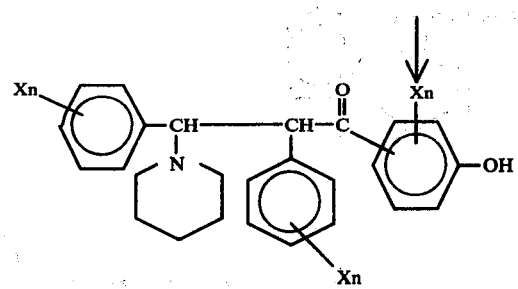

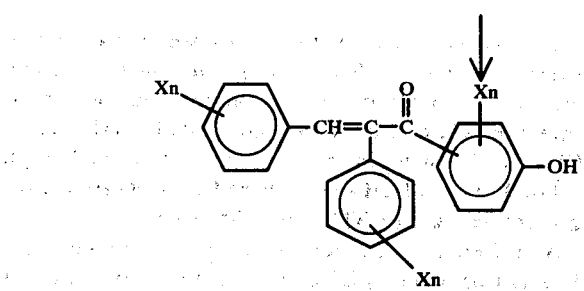

wherein X and n have the same meaning as before.

The compounds of the invention where R is H are conveniently prepared by the reaction of a nuclear hydroxy substituted 1,2-diarylethanone with formaldehyde or paraformaldehyde and the acid addition salt of a di-lower alkylamine, piperidine or morpholine and the Mannich amine salt is then converted directly to the nuclear hydroxy substituted 1,2-diphenyl-2-propen-1-one by decomposition, as for example, by heating the Mannich salt at temperatures above room temperature and, preferably, in the presence of a solvent of high dielectric constant such as dimethylformamide or, alternatively, the salt of the Mannich amine is treated with a weak base, such as sodium bicarbonate, to obtain the corresponding free Mannich amine derivative, which is then decomposed to the desired nuclear hydroxy substituted 1,2-diaryl-2-propen-1-one. The following illustrates this method for preparation:

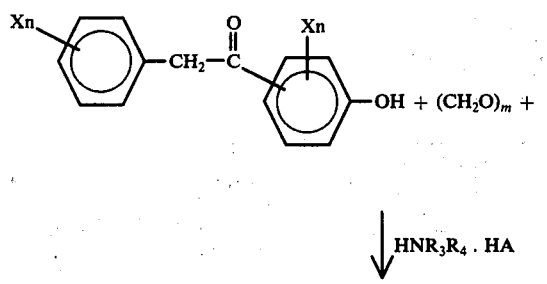

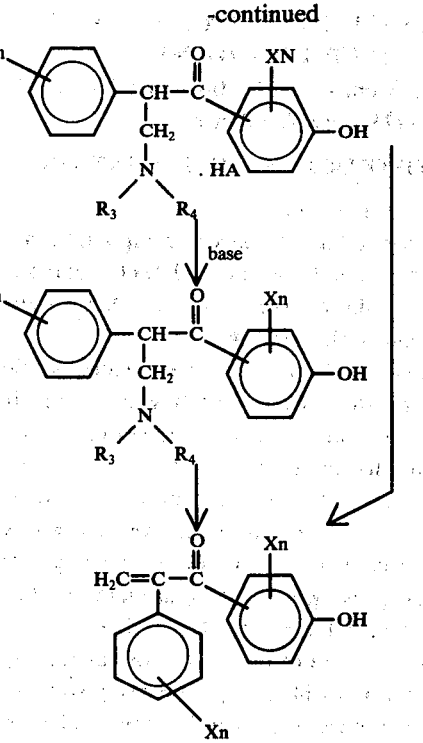

wherein X and n are as defined above, $HNR_3R_4$ is a secondary amine, for example, an amine selected from the group consisting of dilower alkylamine, piperidine and morpholine; HA is the moiety derived from an organic or inorganic acid capable of forming salts with amines, for example, hydrochloric acid, etc. and m is a positive integer of 1 or greater.

An alternate method for preparing the nuclear hydroxy substituted 1,2-diphenyl-2-propen-1-one also comprises treating a nuclear hydroxy substituted 1,2-diarylethanone with formaldehyde or paraformaldehyde and the salt of a secondary amine to obtain the Mannich salt as in the foregoing method. The Mannich salt is then converted to the free Mannich amine which is then treated with a suitable quaternizing agent to obtain the corresponding quaternary ammonium salt and then converting the said quaternary ammonium derivative to the desired nuclear hydroxy 1,2-diaryl-2-propen-1-one by treatment with a base, for example, with an aqueous solution of sodium bicarbonate. The following equation illustrates this method of preparation:

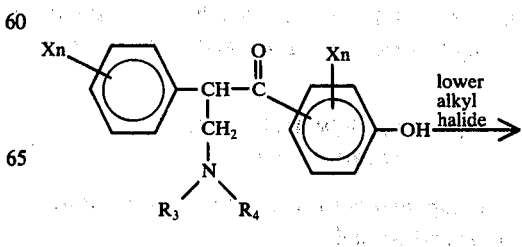

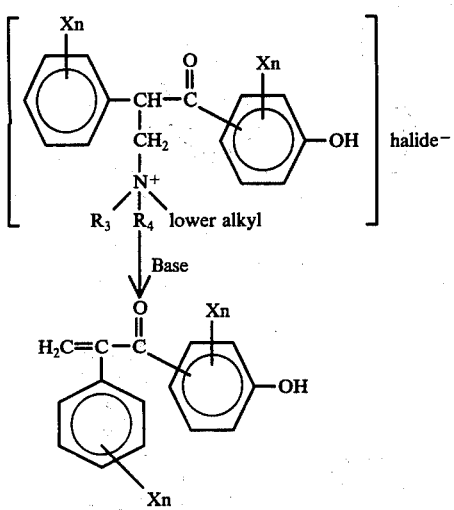

wherein R$_3$, R$_4$, X and n are as defined before.

Another method for preparing nuclear hydroxy substituted 1,2,3-triaryl-2-propen-1-one comprises treating a suitable nuclear hydroxy substituted 1,2,3-triaryl-1-propanone with a halogenating agent, for example, with chlorine, bromine, iodine monochloride, etc., followed by the reaction of the halogenated derivative with a dehydrohalogenating agent. Dehydrohalogenating reagents which are suitable in the process, include, for example, tertiary amines, metal halides, alkali metal acetates, alkali metal carbonates, etc. Specifically triethylamine, anhydrous lithium chloride, lithium bromide, silver acetate, potassium acetate, silver fluoride and potassium carbonate have been found to be particularly effective in the dehydrohalogenation reaction.

In general, the dehydrohalogenation reaction may be carried out in an inert solvent in which all the reactants are reasonably soluble, for example, in dimethylformamide, especially when lithium chloride or lithium bromide is the dehydrohalogenating agent employed. The process is illustrated by the following:

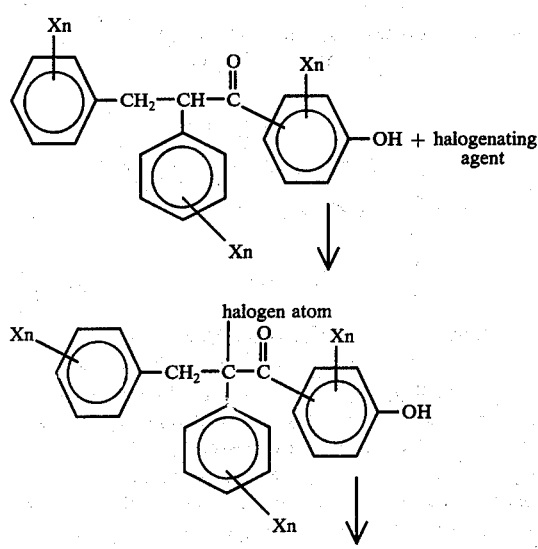

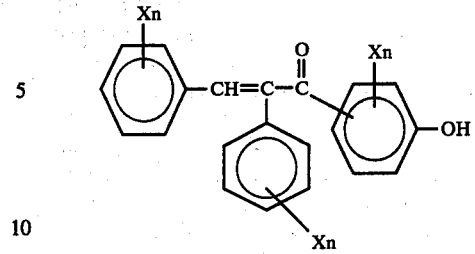

wherein X and n have the same meaning as before.

Another approach to the synthesis of nuclear hydroxy substituted 1,2,3-triaryl-2-propen-1-one is by reacting carbonyl compounds, in the presence of proton acceptors containing metal, with such derivatives of carbonyl compounds as contain a ($>$C=n—) group in place of a ($>$C=O) group and moreover contain a (—CH$_2$—) group vicinal to the imino carbon atom and then dehydrating and hydrolyzing the reaction product.

The process is described below:

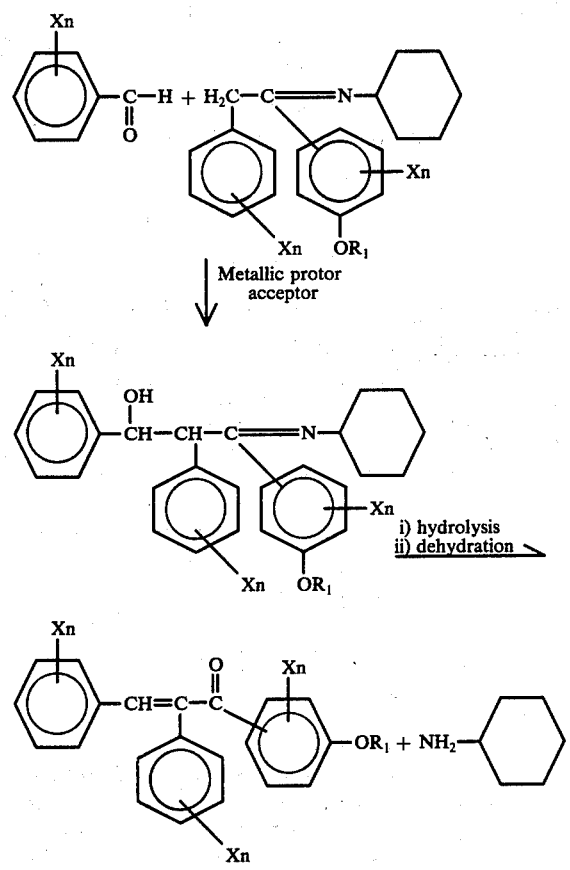

where X, R$_1$ and n have the same meaning as before.

Suitable derivatives of carbonyl compounds in which the C=O group is replaced by a C=N— group and which contain a methylene group vicinal to the imino-carbon atom are the reaction products of nuclear hydroxy or alkoxy substituted 1,2-diarylethanones with aliphatic, cycloaliphatic, araliphatic and aromatic amines, hydrazines or the oxygen derivatives of hydroxylamine.

Suitable metal containing proton acceptors are organic compounds such as lithium methyl, lithium butyl, lithium phenyl, sodium phenyl, alkali acetylene compounds and Grignard compounds. Compounds of the alkali metals with organic amines and ammonia are particularly suitable. Examples of such compounds are lithium amide, sodamide, potassium amide, lithium diisopropylamide, lithium diethylamide, etc.

Preferred solvents for the foregoing reaction are ethers, such as diethylether, tetrahydrofuran, dioxane, hydrocarbons, such as hexane, octane, cyclohexane, benzene and toluene and dimethylformamide, n-methylpyrrolidone and dimethylsulfoxide. The reaction is suitably carried out in an inert atmosphere in the range between room temperature and −70° C.

The starting material for all above reactions, the nuclear hydroxy substituted 1,2-diaryl-ethanones can be conveniently prepared by Friedel-Crafts method by reacting appropriately substituted aryl acetyl chloride with excess alkoxybenzene in presence of a catalyst, for example, anhydrous aluminium chloride, followed by demethylation of the alkyl ether. Pyridine-hydrochloride, anhydrous aluminium chloride or boron trihalides are preferred as dealkylating agents. Methoxy- or ethoxybenzenes are preferably used. The process is outlined below:

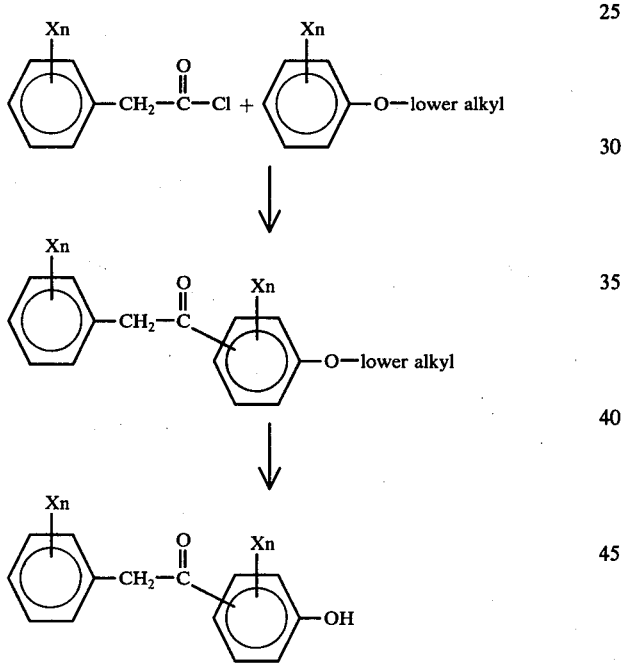

wherein X and n are as indicated before.

It frequently occurs that the foregoing Friedel-Crafts reaction produces a mixture of the 2- and 4-isomers of the ethers, as for example, when the phenol ether employed has a 3-chloro or 3-methyl substituent. In such an instance, they are separated by fractional distillation of the nuclear hydroxy derivatives obtained after dealkylation and may then be etherified if necessary by conventional means to the corresponding pure ether compounds.

The nuclear hydroxy substituted 1,2,3-triaryl-1-propanone, used as starting materials, are conveniently prepared by alkylation of a nuclear alkoxy substituted 1,2-diarylethanone obtained before in presence of a base. Suitable alkylating agents are aralkyl halides, such as α-chlorotoluene, α,4-dibromotoluene, etc. Preferred base is potassium tertiary butoxide and preferred solvent is dimethylsulfoxide. Cleavage of the ether linkage gives the desired 1-propanone derivatives as outlined in the following:

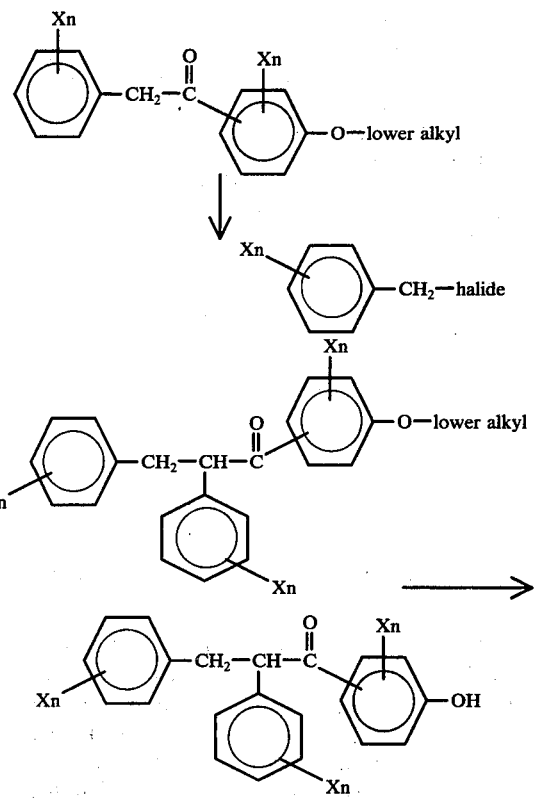

wherein X and n have the same meaning as before.

The examples which follow illustrate the 1-(4-hydroxyphenyl)-2-phenyl-2-propen-1-ones of this invention and the method by which they are prepared. However, the examples are illustrative only and it should be apparent to one having only ordinary skill in the art that all of the products embraced by the general formula, supra, may also be prepared in an analogous manner by substituting the appropriate starting materials for those set forth in the examples. All temperatures are in degrees centigrade.

EXAMPLE 1

Method of making 1-(4-hydroxyphenyl)-2,3-diphenyl-2-propen-1-one having the structural formula

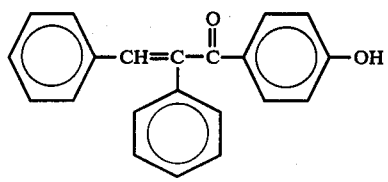

A. 9 g (0.0424 moles) 1-(4-hydroxyphenyl)-2-phenylethanone, 4,5 g (0.0424 moles) benzaldehyde, 3.38 g (0.0397 moles) piperidine and 18 ml methanol were combined and let stir for about 3 hours at room temperature. By this time the mixture had solidified. After keeping overnight, the solid was filtered and washed with a small amount of methanol. After drying 11.5 g (70%) of a grey powder with m.p. 144°–147° was obtained.

B. 10 g (0.0259 moles) of this material was combined with 110 ml glacial acetic acid and the mixture refluxed for 4½ hours. After cooling, this was diluted to 650 ml with water whereupon a brown powder precipitated. This was filtered off and dried. One recrystallization from methanol/water gave 4.2 g (54%) of a light brown powder. M.P. 186°-190°.

IR (Nujol): 3440, 1638, 1600, 1580, 1508, 1321, 1307, 1282, 1267, 1233, 1187, 1170, 1109, 1086, 1065, 1028, 930, 920, 878, 852, 838, 774, 767, 718, 692 cms$^{-1}$.

NMR (Acetone-[$_6$ + tms); 7.9 δ (doublet); 7.24 δ (singlet); 7.2 δ (singlet); 6.8 - 7.2 δ (multiplet).

EXAMPLE 2

Method of making 1-(4-hydroxyphenyl)-3-(4-chlorophenyl)-2-phenyl-2-propen-1-one having the structural formula

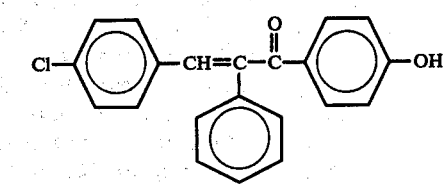

9.4 g (0.0443 mole) of 1-(4-hydroxyphenyl)-2-phenylethanone, 6.23 g (0.0443 mole) of 4-chlorobenzaldehyde and 3.53 g (0.0415 mole) of piperidine in 19.3 ml of methanol was stirred at 35° and then kept overnight. It was worked up as under Example IA to give 14.5 g (83%) of crude product. 14 g (0.0333 mole) of the crude phenol was mixed with 140 ml of glacial acetic acid and refluxed for 4 hours. Work up as under Example IB followed by recrystallization from methanol gave 3.7 g (34%) of pure product, m.p. 179°-181°.

NMR (D$_6$-Acetone + TMS): 8.2 - 8.4 δ (doublet); 7.1 - 7.7 δ (multiplet).

IR(Nujol): 3460, 1638, 1602, 1581, 1510, 1488, 1405, 1310, 1280, 1263, 1236, 1170, 1109, 1092, 1067, 1013, 952, 920, 910, 880, 852, 823, 769, 730, 717, 710 and 699 cm$^{+1}$.

EXAMPLE 3

Method of making 1-(4-hydroxyphenyl)-3-(4-bromophenyl)-2-phenyl-2-propen-1-one having the structural formula

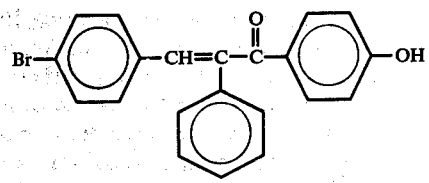

8.02 g (0.0378 mole) of 1-(4-hydroxyphenyl)-2-phenylethanone, 7.0 g (0.0378 mole) of 4-bromobenzaldehyde, 3.01 g (0.0353 mole) of piperidine and 16.5 ml of methanol was treated or mentioned under Example IA to give 13 g (74%) of crude product. 12.5 g (0.027 mole) of this phenol was refluxed with 120 ml and worked up as in Example IB. Recrystallization from methanol gave 5.2 g (51%) of the product.

IR (Nujol) 3460, 1637, 1601, 1581, 1510, 1485, 1400, 1310, 1280, 1262, 1233, 1169, 1108, 1073, 1065, 1010, 920, 910, 880, 853, 820, 768, 728 cms$^{-1}$.

NMR (D$_6$-Acetone + TMS): 8.1 - 8.3 δ (doublet); 7.25 - 7.9 δ (multiplet).

EXAMPLE 4

Method of making 1-(4-hydroxyphenyl)-2-(4-chlorophenyl)-3-phenyl-2-propen-1-one having the structural formula

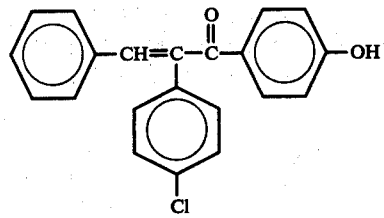

8 g (0.0324 mole) of 1-(4-hydroxyphenyl)-2-(4-chlorophenyl)ethanone (prepared by Friedel-Craft reaction between methoxybenzene and 4-chlorophenylacetylchloride, followed by demethylation of the methyl ether with pyridine hydrochloride) was treated with 3.44 g (0.0324 mole) of benzaldehyde and 2.58 g (0.304 mole) of piperidine in 15 ml of methanol at 60° C and worked up as under Example IA gave 9.0 g of crude product. 8.5 g of this material on refluxing with 85 ml of glacial acetic acid for 4 hours and was worked up as under Example IB. Trituration with hot methanol and cooling gave 3 g (44.5%) of crystalline material, m.p. 228°.

IR (Nujol): 3465, 1632, 1600, 1578, 1508, 1278, 1263, 1225, 1170, 1088, 1013, 883, 845, 793, 770, 740, and 720 cms$^{-1}$.

NMR (D$_6$-Acetone + TMS): 8.1 - 8.3 δ (doublet); 7.1 - 7.3 δ (doublet); 7.4 - 7.6 δ (multiplet).

EXAMPLE 5

Method of making 1-(4-hydroxyphenyl)-2-(4-bromophenyl)-3-phenyl-2-propen-1-one, having the structural formula

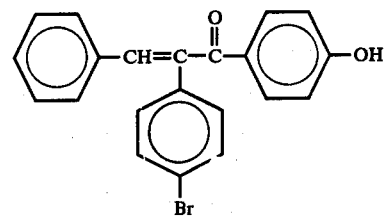

10 g (0.0343 mole) of 1-(4-hydoxyphenyl)-2-(4-bromophenyl)ethanone (prepared from 4-bromophenylacetylchoride and methoxybenzene followed by demethylation with pyridine hydrochloride), 3.65 g (0.0343 mole) of benzaldehyde, 2.75 g (0.0325 mole) of piperidine in 15 ml of methanol at 50° gave 4.9 g (31%) of yellowish white solid. Evaporation of the mother liquor gave 10 g of foamy material which showed 3 spots on TLC. The major spot was identical with the pure product.

4.8 g (0.0103 mole) of this material was refluxed with 100 ml of acetic acid for 4 hours. Work up as in the previous examples, followed by recrystallization from warm methanol gave 1.1 g (28%) of the desired product.

10 g of the foamy material gave additional 1.8 g (22%) of pure phenol derivative on hydrolysis.

IR (Nujol): 3344, 1637, 1608, 1575, 1513, 1488, 1361, 1314, 1280, 1264, 1227, 1167, 1081, 1070, 1058, 1009, 939, 913, 881, 851, 833, 813, 793, 764, 740, 719, 709, 699 and 687 cms$^{-1}$.

NMR (D$_6$-Acetone + TMS): 8.1 – 8.3 δ (doublet); 7.1 – 7.3 δ (doublet); 7.4 – 7.9 δ (multiplet).

EXAMPLE 6

Method of making 1-(4-hydroxyphenyl)-2,3-di(4-chlorophenyl)-2-propen-1-one, having the structural formula

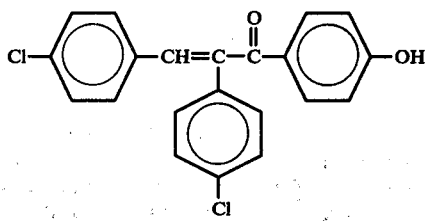

8 g (0.0324 mole) of 1-(4-hydroxyphenyl)-2-(4-chlorophenyl)ethanone, 4.56 g (0.0324 mole) of 4-chlorobenzaldehyde, 2.58 g (0.0302 mole) of piperidine in 14.2 ml of methanol was stirred at 60° overnight and worked up as in previous examples to give 10.5 g (71%) of crude product.

10 g (0.022 mole) of this crude material was refluxed with 100 ml of acetic acid for 4 hours and worked up as before. Yield 5.5 g (68%), m.p. 132°–136°.

I.R. (Nujol): 3467, 1633, 1601, 1579, 1510, 1488, 1310, 1278, 1263, 1230, 1171, 1088, 1067, 1013, 887, 860, 845, 825, 798 and 765 cms$^{-1}$.

NMR (D$_6$-DMSO + TMS): 8.1 – 8.3 δ (doublet); 7.1 – 7.3 δ (doublet); 7.4 – 7.8 δ (multiplet).

EXAMPLE 7

Method of making 1-(4-hydroxyphenyl)-3-(4-nitrophenyl)-2-phenyl-2-phenyl-2-propen-1-one, having the structural formula

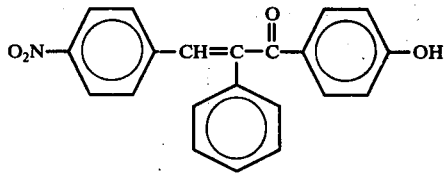

5 g (0.0235 mole) of 1-(4-hydroxyphenyl)-2-phenylethanone, 3.56 g (0.0235 mole) of 4-nitrobenzaldehyde and 1.88 g (0.0221 mole) of piperidine in 10 ml of methanol on stirring overnight at room temperature gave a yellow solid, m.p. 153°–157°. This solid was taken in 100 ml of glacial acetic acid and refluxed for 4½ hours. The resultant clear yellow solution was poured into 700 ml of cold water. The resulting oil was extracted into chloroform, chloroform solution washed with water, dried and concentrated. An orange oil was obtained which slowly crystallized. This material upon purification through column chromatography and recrystallization afforded pure product. M.P. 173°–177°.

NMR (D$_6$-Acetone): 8.1 – 8.4 δ (multiplet); 7.7 δ (singlet); 7.55 δ (singlet); 7.05 – 7.4 δ (triplet).

IR (Nujol): 3360, 1640, 1608, 1580, 1520, 1495, 1420, 1358, 1318, 1292, 1280, 1225, 1175, 1120, 1082, 1074, 905, 900, 860, 780, 770, 760, 730, 720, 710, 680, 620, 605 cms$^{-1}$.

EXAMPLE 8

Method of making 1-(4-hydroxyphenyl)-3-(4-aminophenyl)-2-phenyl-2-propen-1-one having the structural formula

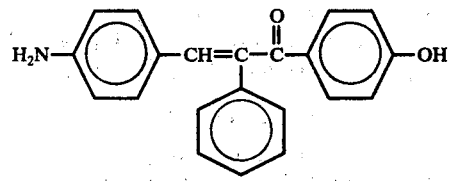

540 mg (0.00146 mole) of the material obtained under Example 7 was taken in 1 ml of ethanol and 1.5 ml of 37% hydrochloric acid. A solution of 1.13 g (0.005 mole) of stannous chloride in 4 ml of ethanol was added dropwise. The stirred mixture was refluxed for 1 hour and the solution was concentrated to a dark red oil. The oil was washed with saturated sodium bicarbonate solution and was extracted with chloroform. Chloroform solution was washed with water, dried and concentrated to give 430 mg of orange red material. This material was homogeneous on TLC.

IR (Nujol): 3370, 1635, 1580, 1545, 1515, 1310, 1280, 1235, 1190, 1165, 910, 830, 760, 700 cm$^{-1}$.

NMR (CDCl$_3$): δ 7.9 – 8.2 doublet; δ 6.4 – 7.7 multiplet; δ 4.5 – 5.5 broad singlet.

EXAMPLE 9

Method of making 1-(4-hydroxyphenyl)-2-phenyl-2-propen-1-one, having the structural formula

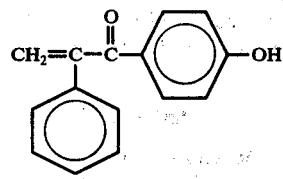

15 g (0.0707 mole) of 1-(4-hydroxyphenyl)-2-phenylethanone, 2.8 g (0.0897 mole) of paraformaldehyde, 7.7 g (0.0912 mole) of dimethylamine hydrochloride, 15 ml of ethanol and 0.3 ml of concentrated hydrochloric acid were combined, refluxed and filtered on cooling. 2 g of this solid was mixed with 100 ml of saturated sodium bicarbonate solution and the suspension was heated for 3 hours at 80°. After cooling the mixture was acidified, extracted with ether and concentrated to an oil which solidified. This material was passed through a silica gel column to obtain 70% pure product, the contaminant being the starting the ethanone derivative. The crude product was obtained in 13% yield after several recrystallizations.

IR (Nujol): 3344, 1675, 1642, 1608, 1575, 1515, 1494, 1340, 1332, 1282, 1217, 1163, 1109, 1074, 1024, 988, 966, 952, 855, 840, 800, 794, 775, 727 and 704 cm$^{-1}$.

NMR (CDCl$_3$ + TMS): δ 8.0 – 8.25 multiplet; δ 7.4 – 7.65 multiplet; δ 6.9 – 7.25 multiplet; δ 6.25 singlet; δ 5.7 singlet.

EXAMPLE 10

In Vitro Prostaglandin Dehydrogenase Assay

A number of compounds were tested for their prostaglandin dehydrogenase inhibition activity.

The prostaglandin dehydrogenase enzyme was prepared from swine lung by homogenization followed by differential centrifugation to obtain the 105,000 × x g supernatant. The supernatant was fractionated by ammonium sulfate with the 20-45% saturation fraction being saved. This fraction was adsorbed to Cellex-T and subsequently eluted with 0.3M KCl. The eluted fraction was concentrated and stored at −20° C as an ammonium sulfate suspension. The enzyme specific activity was approximately 100 p moles of NADH generated per minute per mg of protein.

Assay

400 – 500 μg of protein was incubated at 37° C with Tris HCl (pH-8.2), 50 mM KCl, 10 mM $MgCl_2$, 7 mM 2-mercaptoethanol, 250 μM $NAD^+$, 90 μM $PGE_1$ and the inhibitor under study in a total volume of 1.0 ml. All of the above components except $PGE_1$ and the inhibitor were mixed and allowed to incubate for 15 minutes at 37° C. The fluorescent emission at 460 nm (excitation at 340 nm) was measured during the last few minutes in order to establish a baseline. The $PGE_1$ (and inhibitor) was then added and the reaction monitored by following the increased fluorescence due to NADH production.

Results

The following table summarizes the results obtained with the subject compounds in terms of an $I.D._{50}$.

| Compound | Structure | $I.D._{50}$ |
|---|---|---|
| 1 | Ph-CH=C(Ph)-C(O)-C6H4-OH | 20 μM |
| 2 | $NO_2$-C6H4-CH=C(Ph)-C(O)-C6H4-OH | 16 μM |
| 3 | Cl-C6H4-CH=C(Ph)-C(O)-C6H4-OH | 25 μM |
| 4 | Br-C6H4-CH=C(Ph)-C(O)-C6H4-OH | 25 M |
| 5 | Cl-C6H4-CH=C(C6H4-Cl)-C(O)-C6H4-OH | 50 μM |
| 6 | Ph-CH=C(C6H4-Br)-C(O)-C6H4-OH | 40 μM |
| 7 | Ph-CH=C(C6H4-Cl)-C(O)-C6H4-OH | 60 μM |
| 8 | HCl·$H_2N$-C6H4-CH=C(Ph)-C(O)-Ph | 46 μM |
| 9 | $H_2C$=C(Ph)-C(O)-C6H4-OH | 27 μM |

The foregoing Example shows that the subject compounds have excellent prostaglandin dehydrogenase blocking activity.

EXAMPLE 11

Several antihypertensive experiments were carried out using normal, healthy 2-3 Kg cats. The animals were placed under general anesthesia and the cardiac rate and blood pressure were continuously monitored.

A. One mg/Kg of Compound 1 of Example 10 was administered to the test animals (i.v. in 5% gum arabic) every 10 minutes. The results of the study indicated that the test compounds lowered blood pressure at a dose level of 4 mg/Kg, i.e. had a hypotensive effect, which became greater as additional amounts of the test compound were administered.

B. 15 μg of prostaglandin $E_2$ was administered, causing a 20% decrease in the test animals' blood pressure for about 1 minute.

C. 3 mg/Kg of the test compound used in A. above was administered to the test animals, causing no effect, confirming the study shown in A.

D. Experiments B and C above were combined, that is, 3 mg/Kg of the test compound was administered just prior to a dose of 15 μg of prostaglandin $E_2$, resulting in the test animals' blood pressure being lowered about 20% for about 3½ – 11 minutes (two experiments). Additional prostaglandin $E_2$ dosing was also found to be potentiated for up to 30 minutes following the single dose of the subject compound.

Example 11 shows that the subject compounds have a cardiovascular effect and that they protentiate the cardiovascular effects of exogenous prostaglandins.

We claim:

1. A method for inhibiting the activity of 15-OH prostaglandin dehydrogenase in humans or animals comprising administering to a human or animal an effective amount of a compound having the structural formula

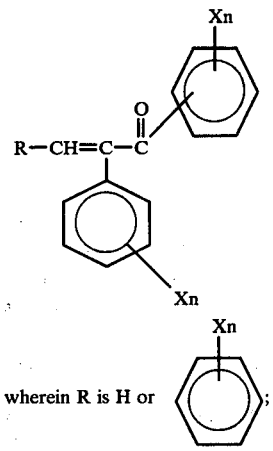

wherein R is H or 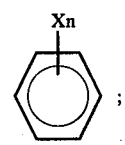;

X is selected from the group consisting of OH, lower alkyl, lower alkoxy, aryl, substituted aryl, halogen, nitro, trihaloalkyl, —NR₁R₂ and —NHCOR₁ where R₁ and R₂ are selected from the group consisting of H, lower alkyl and NH₂; and n is 0-5.

2. A method for inhibiting the activity of 15—OH prostaglandin dehydrogenase in humans or animals comprising administering to a human or animal an effective amount of a compound having the structural formula

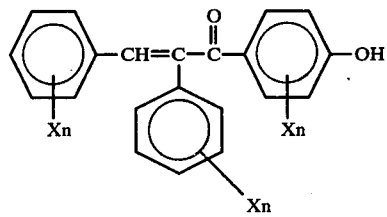

wherein X is selected from the group consisting of H, halogen, NO₂, CF₃, lower alkyl and amino, and n is 0-5.

3. A method for inhibiting the activity of 15—OH prostaglandin dehydrogenase in humans or animals comprising administering to a human or animal an effective amount of a compound having the structural formula

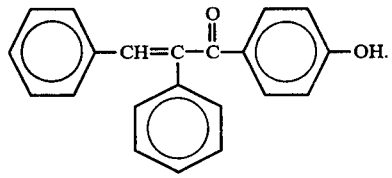

4. A method of lowering blood pressure in humans and animals comprising administering to a human or animal an effective amount of a compound having the structural formula

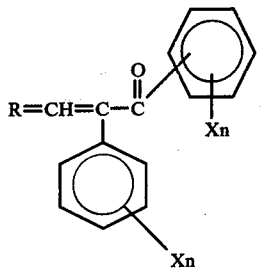

wherein R is H or

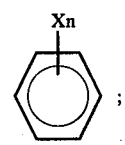;

X is selected from the group consisting of OH, lower alkyl, lower alkoxy, aryl, substituted aryl, halogen, nitro, trihaloalkyl, —NR₁R₂ and —NHCOR₁ where R₁ and R₂ are selected from the grup consisting of H, lower alkyl and NH₂; and n is 0-5.

5. A method of lowering blood pressure in humans and animals comprising administering to a human or animal an effective amount of a compound having the structural formula

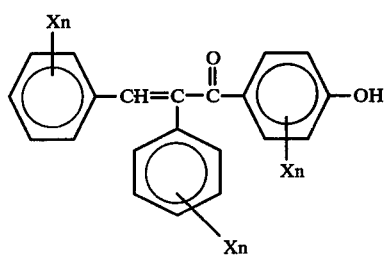

wherein X is selected from the group consisting of H, halogen, NO₂, CF₃, lower alkyl and amino, and n is 0-5.

6. A method of lowering blood pressure in humans and animals comprising administering to a human or animal an effective amount of a compound having the structural formula

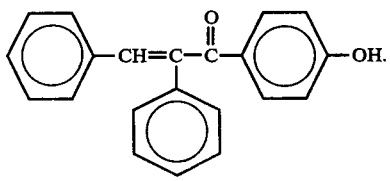

7. A method for potentiating the effects of an exogenously introduced prostaglandin in humans and animals comprising co-administering to a human or animal a prostaglandin and an effective, potentiating amount of a compound having the structural formula

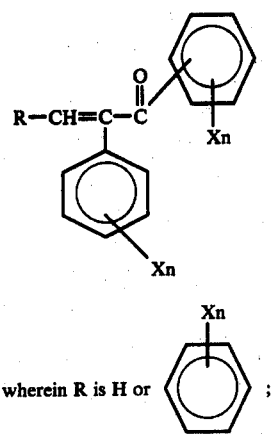

wherein R is H or [phenyl];

X is selected from the group consisting of H, OH, lower alkyl, lower alkoxy, aryl, substituted aryl, halogen, nitro, trihaloalkyl, $-NR_1R_2$ and $-NHCOR_1$ where $R_1$ and $R_2$ are selected from the group consisting of H, lower alkyl and $NH_2$; and $n$ is 0–5.

8. The method of claim 12 wherein the prostaglandin is prostaglandin $E_2$.

9. A method of potentiating the effects of an exogenously introduced prostaglandin in humans and animals comprising co-administering to a human or animal a prostaglandin and an effective, potentiating amount of a compound having the structural formula

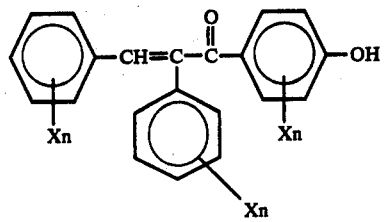

wherein X is selected from the group consisting of H, halogen, $NO_2$, $CF_3$, lower alkyl and amino, and $n$ is 0–5.

10. The method of claim 9 wherein the prostaglandin is prostaglandin $E_2$.

11. A method for potentiating the effects of an exogenously introduced prostaglandin in humans and animals comprising co-administering to a human or animal or a prostaglandin and an effective, potentiating amount of a compound having the structural formula

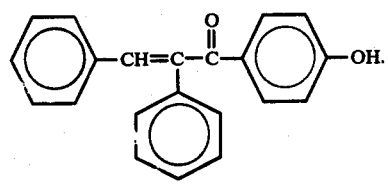

12. The method of claim 11 wherein the prostaglandin is prostaglandin $E_2$.

* * * * *